(12) United States Patent
Hosemann

(10) Patent No.: US 12,408,886 B2
(45) Date of Patent: Sep. 9, 2025

(54) DETECTOR APPARATUS FOR A MEDICAL IMAGING DEVICE

(71) Applicant: Siemens Healthcare GmbH, Erlangen (DE)

(72) Inventor: Michael Hosemann, Erlangen (DE)

(73) Assignee: Siemens Healthineers AG, Forchheim (DE)

( * ) Notice: Subject to any disclaimer, the term of this patent is extended or adjusted under 35 U.S.C. 154(b) by 176 days.

(21) Appl. No.: 18/524,198

(22) Filed: Nov. 30, 2023

(65) Prior Publication Data

US 2024/0215940 A1  Jul. 4, 2024

(30) Foreign Application Priority Data

Dec. 30, 2022 (DE) ............... 10 2022 214 455.4

(51) Int. Cl.
 *A61B 6/03*  (2006.01)
 *A61B 6/00*  (2006.01)
 *A61B 6/42*  (2024.01)
 *G01N 23/046* (2018.01)

(52) U.S. Cl.
 CPC ........... *A61B 6/56* (2013.01); *A61B 6/032* (2013.01); *A61B 6/4233* (2013.01); *G01N 23/046* (2013.01); *G01N 2223/304* (2013.01)

(58) Field of Classification Search
 CPC .. A61B 6/032; A61B 6/03; A61B 6/56; A61B 6/566; A61B 6/42; A61B 6/4233; A61B 6/4266; A61B 6/4283; G01N 23/046; G01N 2223/50; G01N 2223/501; G01N 2223/5015
 See application file for complete search history.

(56) References Cited

U.S. PATENT DOCUMENTS

| | | | |
|---|---|---|---|
| 2006/0067474 A1 | 3/2006 | Schmitt | |
| 2008/0272296 A1 | 11/2008 | Frach | |
| 2016/0256129 A1 | 9/2016 | Ergler | |
| 2024/0215940 A1* | 7/2024 | Hosemann | ............ A61B 6/032 |

FOREIGN PATENT DOCUMENTS

| | | |
|---|---|---|
| DE | 102004048215 A1 | 4/2006 |
| DE | 102015203764 A1 | 9/2016 |

* cited by examiner

*Primary Examiner* — Don K Wong
(74) *Attorney, Agent, or Firm* — Lempia Summerfield Katz LLC

(57) ABSTRACT

A detector apparatus for a computed tomography device includes: at least one detector module having a sensor configured to detect measurement signals; at least one radio unit assigned to the at least one detector module, the radio unit having at least one radio antenna for wireless data transmission of the detector signals; and a housing that at least partially encloses the at least one detector module. The housing has a recess for the at least one radio antenna, relative to which the at least one radio antenna is arranged, so that wireless data transmission of the detector signals through the housing is enabled.

18 Claims, 4 Drawing Sheets

DETECTOR APPARATUS FOR A MEDICAL IMAGING DEVICE

The present patent document claims the benefit of German Patent Application No. 10 2022 214 455.4, filed Dec. 30, 2022, which is hereby incorporated by reference in its entirety.

TECHNICAL FIELD

The disclosure relates to a detector apparatus for a medical imaging device and a computed tomography device including such a detector apparatus.

BACKGROUND

Computed tomography (CT) devices are generally known. It is also generally known that large amounts of data are generated in the rotating part of a CT device, which is transmitted to the stationary part. In particular, the detector data generated in one or more detectors rotating around the system axis of the CT device is transmitted promptly for evaluation.

Currently, data transmission may be carried out using slip ring systems that establish a data transmission path via a capacitive coupling between the rotating and stationary parts. However, this technology may reach its limits if the amount of data to be transmitted continues to increase in the future as detectors are further developed. For example, the data transmission requirements of counting detectors, which have a much finer pixelation and also have several energy thresholds per pixel, further increasing the amount of data to be transmitted, have increased significantly compared to conventional detectors. Furthermore, such a system may be susceptible to performance losses due to wear and contamination. Wireless data transmission of the detector data from the detector apparatus may lead to an improvement here.

A detector in a CT device may include a housing that protects the internal components and shields the components electromagnetically to a large extent, (apart from the desired incident X-ray radiation on a sensor surface of the detector), so that radio transmission out of the housing is difficult.

SUMMARY AND DESCRIPTION

The object of the disclosure is to provide a detector apparatus for a computed tomography device that enables improved wireless data transmission.

The scope of the present disclosure is defined solely by the appended claims and is not affected to any degree by the statements within this summary. The present embodiments may obviate one or more of the drawbacks or limitations in the related art.

The disclosure relates to a detector apparatus for a computed tomography device. The detector apparatus includes: at least one detector module including a sensor for detecting measurement signals; at least one radio unit assigned to the detector module, having at least one radio antenna for wireless data transmission of the measurement signals from the detector module; and a housing which at least partially encloses a detector module, wherein the housing has a recess for the at least one radio antenna, relative to which the at least one radio antenna is arranged, so that wireless data transmission of the detector signals through the housing is enabled.

In particular, the detector apparatus may also have a plurality of detector modules. The plurality of detector modules may be arranged next to each other in such a way that the sensor units together act as a larger detection surface.

In particular, a detector module includes the sensor and module electronics. The sensor includes a sensor unit having a direct-converting or an indirect-converting converter material and subsequent sensor electronics, e.g., at least one readout unit which detects and at least digitizes the signals generated by the sensor unit in response to incident radiation. The X-rays or X-ray photons may be converted into electrical signals in direct-converting sensor units using a suitable converter material. For example, CdTe, CZT, CdZnTeSe, CdTeSe, CdMnTe, InP, $TlBr_2$, $HgI_2$, GaAs or other materials may be used as converter material. The X-rays or photons may be converted into light in indirect-converting sensor units using a suitable converter material and into electrical pulses using optically coupled photodiodes, in particular a photodiode array. Scintillators, (e.g., GOS ($Gd_2O_2S$), CsJ, YGO or LuTAG), may be used as the converter material here. The module electronics include further electronic assemblies that are necessary for the operation and readout of the detector module, for example, for supplying an operating voltage or actuation signals. For example, the module electronics include a substrate, (e.g., in the form of a printed circuit board), and passive and/or active components and electrical lines arranged on the substrate for operating the detector module.

The detector module may also include further components such as an anti-scatter grid, a module holder configured for mounting the module in the detector apparatus, or a heat sink.

According to the disclosure, the measurement signals detected by the sensor, (hereinafter also referred to as detector data), are forwarded by the sensor to a radio unit configured to send the detector data by a wireless data transmission method, e.g., by radio technology. The radio unit as a transmitter may work together with a further radio unit placed outside the detector apparatus as a receiver, so that the detector data may be transmitted from the detector module to the further receiver radio module placed outside the detector apparatus. There may also be configurations in which the radio unit of the detector module may be configured as a receiver in order to receive radio signals, (e.g., including actuation signals for the detector module), from a transmitter placed outside the detector apparatus. In this way, actuation signals for the detector module may also be advantageously transmitted by wireless data transmission. Advantageously, further data transmission paths for actuation via a slip ring design may be avoided and cabling costs reduced.

The radio unit includes at least one radio antenna and one radio circuit. In certain examples, the radio unit includes at least one radio circuit in the form of an integrated circuit (IC), also known as a solid-state circuit. In particular, this may be configured as an ASIC (application specific integrated circuit). In advantageous configurations, the radio antenna may be configured as an antenna array.

The radio circuit, together with the radio antenna, is configured to send the detector data, which is forwarded from the sensor to the radio unit, by a wireless data transmission method, (e.g., to transmit the data to a receiver unit). The method of wireless data transmission and the configuration of the radio unit may be selected in such a way that it is suitable for the data transmission of the detector data and is also to be configured to the specific configuration and the specific usage conditions of the detector apparatus. In the case of a detector apparatus in a CT system, for example, requirements regarding data volume and existing interference signals are considered. The positioning of the transmitter relative to the receiver are also considered. An arrangement of a receiver in the stationary part of a CT system, (e.g., in the direct vicinity of the rotor), enables a different implementation than the provision of a receiver at a location outside the CT device, (e.g., separately in the application room), due to a significantly smaller distance between a radio unit of the detector module and the receiver. A wireless data transmission method may use a WLAN (wireless local area network) standard, which may use frequency bands in the 2.4 GHz or 5 GHz range. However, other implementations may also be provided, in particular those that have a low susceptibility to electromagnetic interference signals occurring in the CT device, and a high data rate, and/or also those that are optimized for shorter distances between the transmitter and receiver, if the arrangement in the application device, (e.g., in the CT system), allows this.

The radio unit is assigned to the detector module. The detector module may include the radio unit. For example, the radio unit may be arranged on the module electronics of the detector module. However, the radio unit may also form a separate assembly connected to the detector module via a data line. Integration into the detector module may advantageously favor a compact design and reduce cabling effort and advantageously include short transmission paths for the detector data to the radio unit. A separate arrangement may be favorable if in this way the arrangement of the radio module in the detector apparatus may be optimized for wireless data transmission.

The detector housing at least partially encloses the detector module. The housing is used to protect the internal components and possibly also to enable controllable conditions, for example, for temperature stabilization. The housing may enclose the detector module from all sides or only partially. In particular, the housing at least allows incident X-rays to strike the sensor of the detector module. Furthermore, openings may be provided for the feeding of cables or the supply of cooling air. However, the housing shields the detector module electromagnetically to a large extent (apart from the desired incident X-ray radiation on a sensor surface of the detector), making radio transmission through the housing material more difficult at any rate. The housing may include a metal. The housing may be assembled from a plurality of composite parts. For example, the housing may include a module carrier to which detector modules may be attached. The housing may include covers that may be attached to the module carrier.

In certain examples, the housing has at least one recess assigned to the detector module for the at least one radio antenna of the detector module, relative to which the at least one radio antenna is arranged, so that wireless data transmission of the detector signals through the housing is enabled. The recess is configured to the radio antenna and is configured in such a way that, if the radio antenna is suitably positioned, the wireless data transmission of the detector signals by the radio antenna to a receiver unit is not impaired by the housing, or only to a limited extent.

The radio antenna may be arranged inside the interior space configured by the housing, but in the direct vicinity of the recess, so that radio transmission is possible through the recess. Advantageously, the housing also protects the radio antenna and the data feed line to the radio antenna. However, the radio antenna may also be arranged within the recess. The housing may advantageously reduce the restriction of the radiation directions. The antenna may also be positioned at least partially outside the recess and connected to the detector module or the sensor through the recess. A further optimized arrangement is advantageously possible. In advantageous configurations, however, the radio circuit of the radio unit is arranged within the interior space formed by the housing, so that the radio circuit is protected from interference by the housing.

Advantageously, the detector data may be transferred to a radio unit in the immediate vicinity of its point of origin and the transmission may take place. The transmission paths and intermediate acts are advantageously short. A further advantage is that the radio transmission technology is also widely used outside of X-ray detectors or computed tomography and therefore offers significantly more cost-effective assemblies than, for example, when using slip ring technology. At the same time, wireless data transmission is advantageously not impaired by the housing.

In particular, the detector apparatus may include a plurality of detector modules arranged next to each other, with each detector module of the plurality of these being assigned at least one radio unit and a recess in the housing assigned to it. The plurality of detector modules may be arranged next to each other in the detector apparatus so that the sensors together act as a larger detection surface.

In advantageous embodiments, each detector module used in the detector apparatus has a radio unit so that the detector data generated in a detector module may be transferred directly to the respective radio unit present in this detector module and transmitted directly without any further intermediate acts or paths. In this way, transmission of the data over longer data transmission paths to a sender unit is also avoided. Furthermore, parallel data transmission of the detector data from the modules may enable a particularly high data transmission rate overall. Furthermore, this allows detectors with different numbers of modules to be produced without significant effort in the development of electronic hardware.

In certain examples, a detector apparatus combines detector modules with a radio unit and those without a radio unit, wherein a feed of the detector data from such modules without a radio unit to those with a radio unit is provided. For example, these may be arranged alternately next to each other. Although this increases the amount of data to be transmitted by a radio unit and the amount of cabling required, there may be at least partial cost savings, as a radio unit does not have to be provided in every detector module, wherein parallel data transmission or relatively short transmission paths do not have to be completely dispensed with, however.

According to one embodiment variant of the detector apparatus, the recess is at least partially covered by a material which is designed as permeable for the wireless data transmission of the detector signals. This variant is associated with an arrangement of the radio antenna within the detector housing or, depending on the specific arrangement, with an arrangement within the recess. The material is selected depending on the specific embodiment, in particular the frequencies used for data transmission. In particular, the cover may be selected in such a way that the data transmission is not impaired by the material of the cover, or only impaired to an extent that does not reduce the quality of the transmitted data for subsequent use. However, a cover may advantageously provide protection against contamination, (e.g., the accumulation of dust in the interior of the housing), or the creation of an optimized operating environment for the detector module, because the interior space of the housing is better sealed by the cover, at least in contrast to an uncovered recess, and may reduce an undesired air supply. In other examples, there is no cover. This may also be desirable and may be used for a cooling air supply. In addition, the choice of material may be reduced at lower frequencies so that for improved wireless data transmission a cover may be dispensed with.

According to one embodiment, an area between the radio unit and the housing is electrically sealed by an electrically conductive sealing material. The area relates in particular to edge areas around the recess, e.g., gaps between the edge of the recess and an edge of a radio unit positioned relative to it. However, the recess is not covered by the material that would impair wireless data transmission. An interior space of the detector apparatus is protected from electromagnetic interference that may impair the further processing and transmission of measurement signals in the detector module.

In other embodiments, the gap is configured as an air gap. Advantageously, an assembly act and material may be dispensed with in order to enable more cost-effective provision. Furthermore, the gap may be used as an air supply for cooling.

In a further embodiment, the at least one radio antenna is arranged relative to the recess in such a way that the radio antenna has a distance in a sub-mm range to at least part of the housing, (e.g., a distance of less than 1 mm between the radio antenna and the housing), so that at least this part of the housing may be used as a ground plane for the radio antenna. For example, this arrangement may be achieved by a mechanical assembly made of a dielectric material, which keeps the radio antenna at a tolerated distance relative to the housing in the sub-mm range and also keeps it stable during operation. Advantageously, a suitable ground plane for the radio antenna may be provided by the housing. A combination of this embodiment with a further sealing of gaps using an electrically conductive sealing material is also possible.

In a further embodiment, the radio unit of the detector module is at least partially protected against incident radiation during operation of the detector apparatus, at least along a direction of incidence of the radiation. In particular, the housing may have a suitable housing part or be configured in such a way that protection of the radio unit is provided during operation.

According to a further embodiment, at least one part of the housing has a concave shape that curves into the detector interior space of the detector apparatus formed by the housing. In particular, this may enable an improved relative arrangement of the radio unit to the housing or the recess. Furthermore, the radiation of the radio antenna may be advantageously optimized by avoiding the housing parts restricting it.

According to a further embodiment, the housing of the detector apparatus has a wall thickness taper in a wall area around the recess. Advantageously, a restriction on the radiation of the radio antenna may be further reduced by the housing.

The disclosure further relates to a computed tomography device including a detector apparatus according to one of the variants described above and an X-ray source in opposition thereto, which is configured to expose the detector apparatus to X-rays.

In certain examples, an object to be mapped may be placed between the X-ray source and the detector module or X-ray detector and irradiated by the X-ray source.

All embodiments previously described in the context of the detector apparatus may accordingly also be implemented in the computed tomography device. The description given with regard to the detector module and the advantages described above may accordingly also be transferred to the computed tomography device disclosed herein.

According to one embodiment variant of the computed tomography device, this includes at least one receiver unit that acts together with the radio unit for data transmission, and which is arranged on a stationary part of the computed tomography device.

The receiver unit includes at least one antenna that allows the detector data transmitted by the radio unit to be received and a circuit that allows the detector data to be processed and forwarded. The receiver unit and the radio unit work together during wireless data transmission and are coordinated with each other so that data transmission is enabled. Placing the receiver unit on the stationary part of the CT device is advantageous, as this allows a relatively small and also defined distance to be covered for data transmission. An arrangement outside the CT device firstly involves greater transmission distances and secondly possibly different conditions from application to application, which is considered.

According to one embodiment of the computed tomography device described above, this includes a plurality of receiver units. This may allow parallel data transmission to the plurality of receiver units. Furthermore, it is also conceivable that advantageously in each case the receiver unit that is optimally positioned in relation to a radio module for radio transmission, is used for transmission.

Furthermore, the receiver units may be mounted on the stator in different arrangements in order to achieve optimum and/or alternating reception situations. Examples of this are a ring-shaped arrangement on the stationary part around an axis of rotation of the computed tomography device or an arrangement as a group on the stator.

Within the scope of the disclosure, features that are described in relation to different embodiments of the disclosure may also be combined to form further embodiments of the disclosure. In addition to the embodiments of the disclosure expressly described in this application, many other embodiments of the disclosure are conceivable, at which the person skilled in the art may arrive without leaving the scope of the disclosure, which is predetermined by the claims.

The use of the indefinite article "a" or "an" does not exclude the possibility that the characteristic concerned may be present more than once. The use of the term "having" does not exclude that the terms linked by the term "having" may be identical. For example, the medical imaging device having the medical imaging device. The use of the term "unit" does not exclude that the object to which the term "unit" refers may include several components that are spatially separated from each other.

BRIEF DESCRIPTION OF THE DRAWINGS

In the following, the disclosure is explained by various embodiments with reference to the attached figures. The illustration in the figures is schematic, highly simplified, and not necessarily true to scale. In the figures.

DETAILED DESCRIPTION

Figure 1:
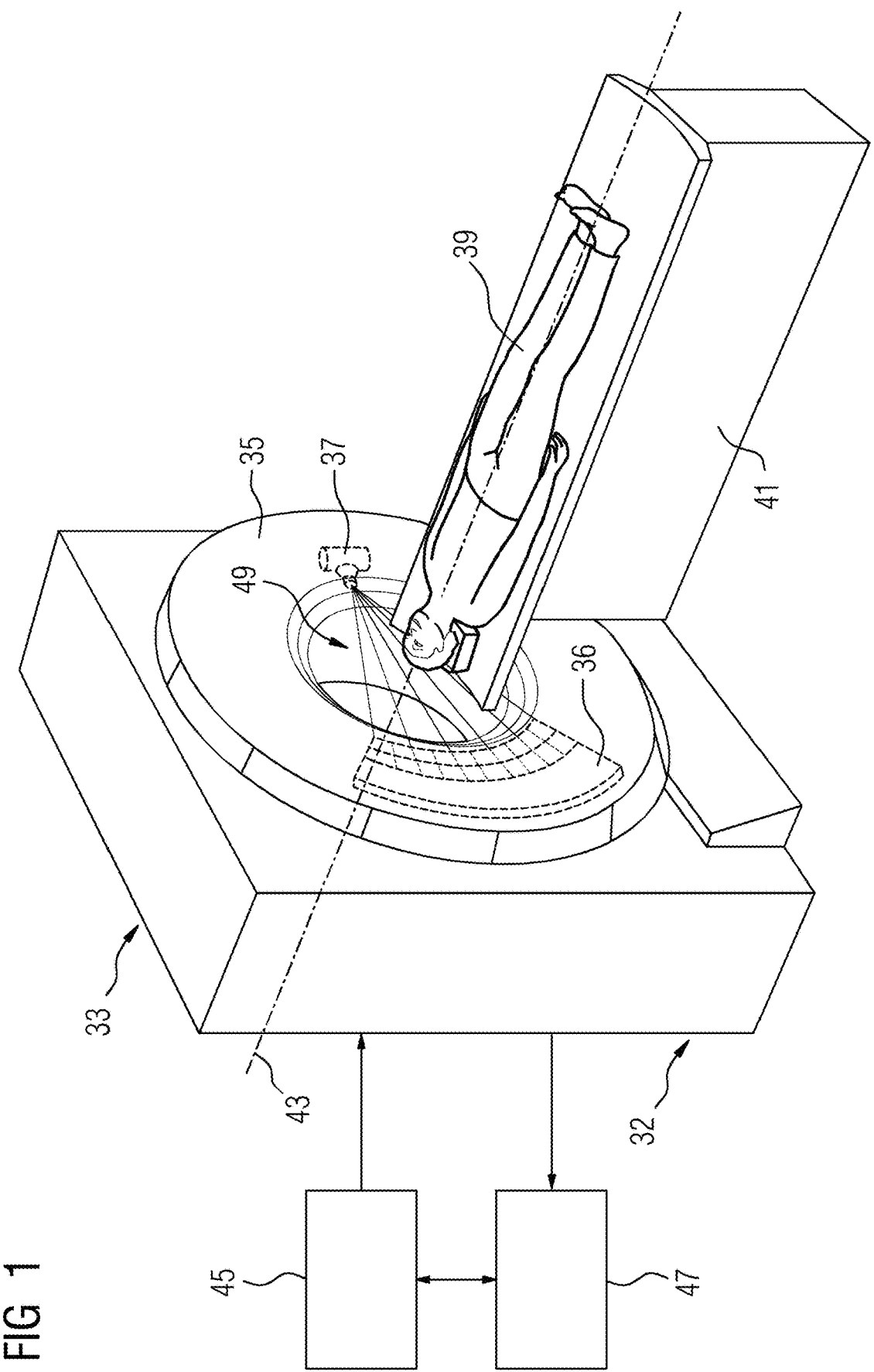
FIG. 1 depicts a schematic representation of an example of a computed tomography device.

FIG. 1 shows an embodiment of a computed tomography device 32 with a detector apparatus 36 and an X-ray source 37 in opposition to the detector apparatus 36. The X-ray source 37 is configured to expose the detector apparatus 36, (e.g., a sensor surface of the detector apparatus 36), with X-rays 49 along a beam incidence direction. The computed tomography device includes a gantry 33 with a rotor 35. The rotor 35 includes the X-ray source 37 and the detector apparatus 36. The rotor 35 is rotatable about the axis of rotation 43. The object to be examined 39, (e.g., a patient), is supported on the patient couch 41 and may be moved along the axis of rotation 43 through the gantry 33. A computing unit 45 is used to actuate the computed tomography device and to calculate sectional images or volume images of the object. The computing unit 45 in the form of a computer system is configured to reconstruct X-ray image data based on the data from the detector apparatus 36 of the computed tomography device. Another computer system serves as an operator console 47. The software installed on the operator console 47 enables the operator to actuate the operation of the computed tomography system, such as selecting a protocol, starting scanning, etc. The operator console 47 may also be configured as a computer system.

A detector apparatus 36 includes at least one detector module 1, (e.g., a plurality of detector modules 1), including a sensor 13 for detecting measurement signals. The detector apparatus 36 further includes at least one radio unit 6 assigned to the detector module 1, having at least one radio antenna 7 for wireless data transmission of the measurement signals. The detector apparatus 36 further includes a housing 3, 11, which at least partially encloses a detector module 1, wherein the housing 3, 11 has a recess 5 for the at least one radio antenna 7, relative to which the at least one radio antenna 7 is arranged, so that wireless data transmission of the detector signals through the housing 3, 11 is enabled. This will be explained in more detail below with reference to the figures that follow.

The computed tomography device 32 also has at least one receiver unit 51 on the stationary part, which acts together with the radio unit 2 of a detector module for wireless data transmission. The receiver unit 51 includes at least one receiver antenna that allows the detector data transmitted by the one radio unit 6 to be received and a circuit that allows the detector data to be processed and forwarded. Placing the receiver unit 51 on the stationary part of the computed tomography device 32 is advantageous, as this allows a relatively small and also defined distance to be covered for data transmission. An arrangement outside the computed tomography device 32 involves greater transmission distances and possibly different conditions and disturbances from application to application, which is taken into account. However, such a placement is also possible.

In advantageous embodiments, the computed tomography device 32 includes a plurality of receiver units 51. These may be mounted on the stator in different arrangements in order to achieve optimum and/or alternating reception situations. Examples of this are a ring-shaped arrangement on the stationary part around the axis of rotation 43 of the computed tomography device 32 or an arrangement as a group on the stator.

Figure 2:
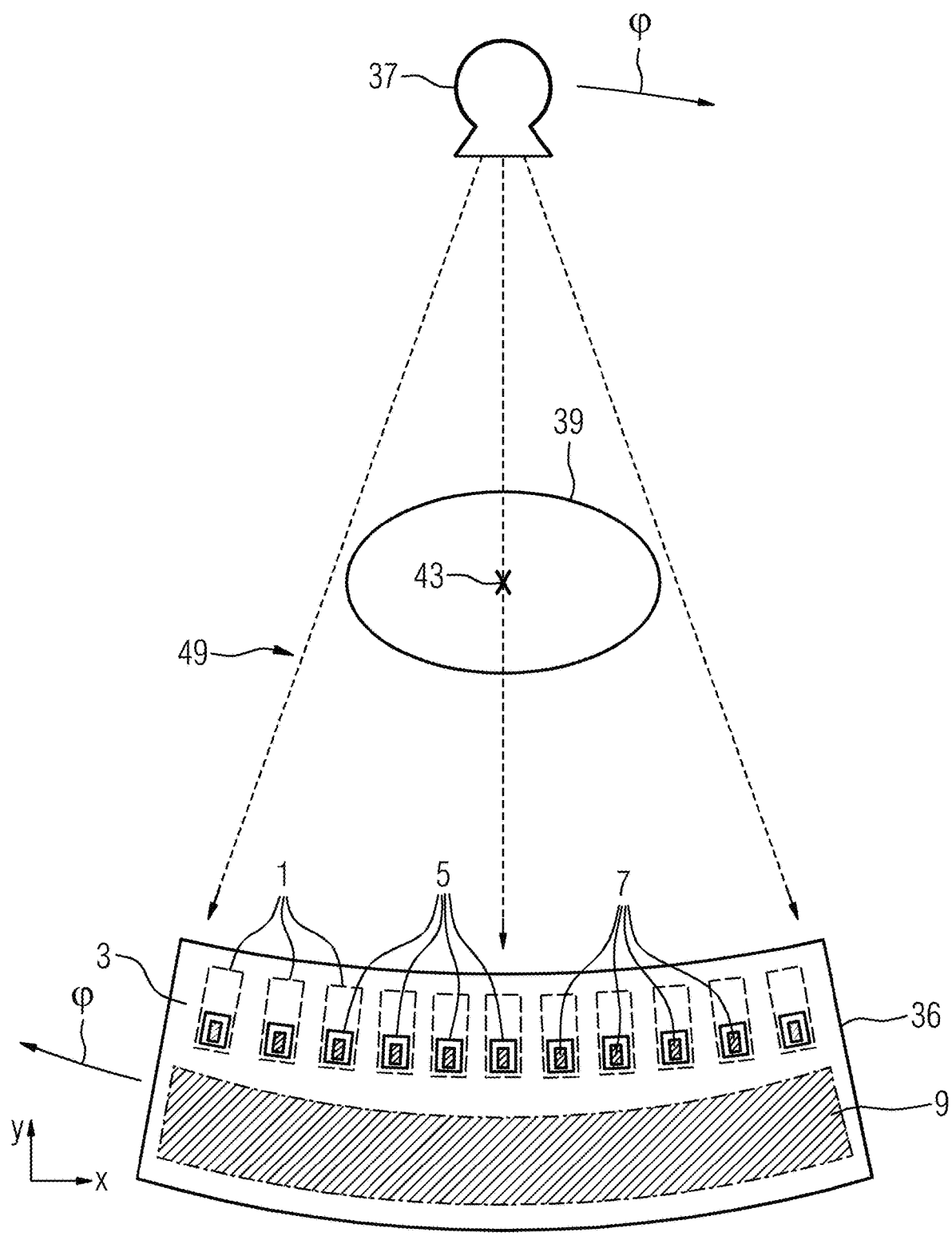
FIG. 2 depicts a schematic representation of an example of an arrangement including a detector apparatus and an X-ray source, as may be present in a computed tomography device.

FIG. 2 is a schematic representation of an arrangement including a detector apparatus 36 and an X-ray source 37, as may be present in a computed tomography device 32, as shown in FIG. 1.

The detector apparatus 36 is shown in a frontal view. The detector apparatus 36 includes a housing, wherein at least one front housing cover 3 is shown here. The housing forms a housing interior space in which a plurality of detector modules 1 (indicated by dashed lines) are arranged. The detector modules are arranged next to each other along the direction of rotation q. The illustration here is understood to be merely schematic. In a specific implementation, the detector modules 1 may be arranged adjacent to each other so that the sensors 13 of the detector modules 1 together act as a larger detection area, wherein a dead area between the sensors 13, which is not sensitive to X-rays, is reduced as far as possible. In the embodiment shown, each detector module 1 of the plurality of the detector modules has at least one radio unit with a radio antenna 7. However, other embodiments are possible.

Furthermore, the housing 3 in each case has a recess 5 assigned to a detector module 1, relative to which the at least one radio antenna 7 of the respective detector module 1 is arranged, so that wireless data transmission of the detector signals by the antenna 7 through the housing 3 is enabled.

The housing 3 may also have other holes, for example, openings may be provided in the housing 3 in an area 9 for the supply or removal of cooling air. However, these openings may be selected in such a way that the housing continues to provide the best possible shielding from electromagnetic signals (apart from the desired incident X-rays on a sensor surface of the detector), wherein interference during operation of the detector apparatus 36 may be avoided. For example, these holes/openings have a diameter of less than 1 cm to prevent the exit or entry of electromagnetic waves in the relevant frequency ranges.

FIG. 3 to FIG. 6 show schematic representations of a cross-section through a detector apparatus 36 for a computed tomography device according to different embodiment variants.

Figure 3:
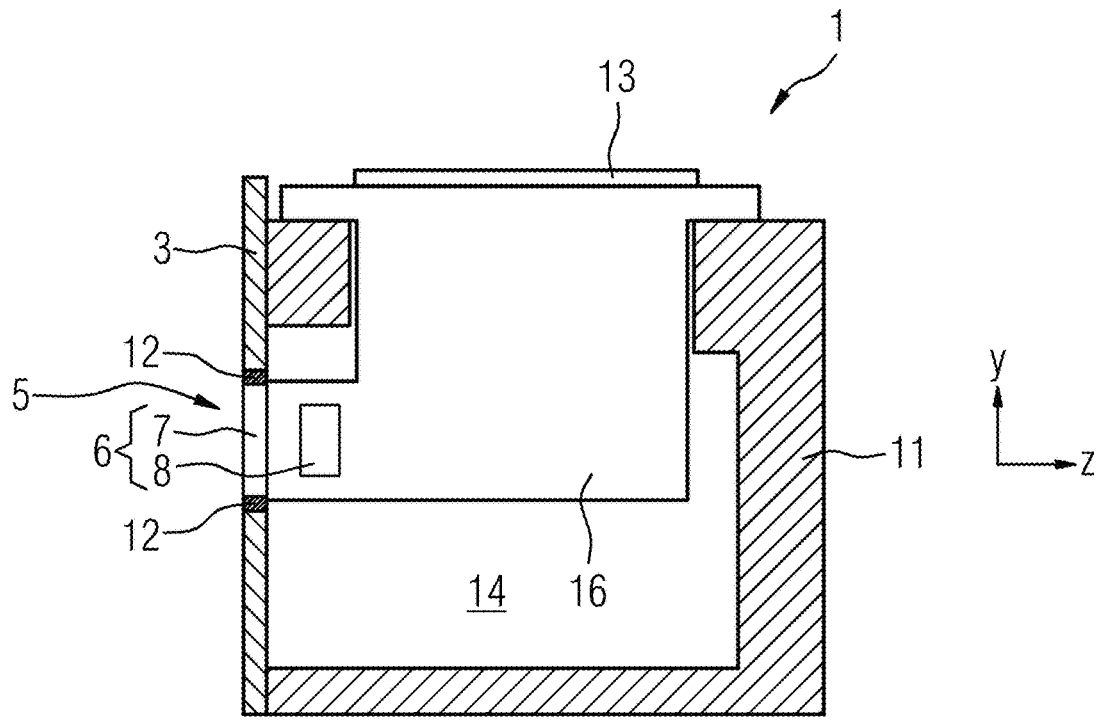
FIG. 3 to FIG. 6 depict schematic representations of a cross-section through a detector apparatus for a computed tomography device according to different embodiment variants.

FIG. 3 schematically shows a detector module 1 with a sensor 13 facing an incident X-ray radiation. The sensor 13 includes a sensor unit having a direct-converting or indirect-converting converter material and subsequent sensor electronics, (e.g., includes at least one readout unit), which detects and at least digitizes the signals generated by the sensor unit in response to incident radiation and forwards them to the radio unit 6. The detector module 1 furthermore includes module electronics 16, which further electronic assemblies that are necessary for the operation and readout of the detector module 1, (e.g., for supplying an operating voltage or actuation signals). For example, the module electronics 16 include a substrate, for example, in the form of a printed circuit board, and passive and/or active components and electrical lines arranged on it for operating and actuating the detector module 1.

The detector module 1 is attached to a module carrier 11. As a rule, the detector module 1 includes a module holder to which the sensor 13 and the module electronics 16 are attached and which is designed for attaching the module 1 to the module carrier 11. However, this is only indicated schematically here, wherein the module holder is not explicitly shown separately from the module electronics 16. The module holder may be made separately from a metal.

The detector module 1 may also include further components, for example, an anti-scatter grid or a heat sink.

In the embodiment shown here, the module carrier 11 along with a cover plate 3 together form the housing 3, 11 of the detector apparatus 36. The housing forms a detector interior space 14. The housing 3, 11 in the depicted embodiment partially encloses the detector module 1, e.g., from all sides apart from a beam entrance side and is used to protect the internal components and possibly also to enable controllable conditions. In other embodiments, the housing may also be configured differently. The housing may include a metal and may be configured to provide extensive shielding of the detector interior space 14.

The detector module 1 further includes a radio unit 6 having a radio circuit 8 and a radio antenna 7, (e.g., a radio antenna array 7). The measurement signals detected by the sensor, (hereinafter also referred to as detector data), are forwarded by the sensor to the radio unit 6 configured to send the detector data by a wireless data transmission method, e.g., by radio technology.

The radio circuit may take the form of an integrated circuit (IC), also known as a solid-state circuit. In particular, this may be configured as an ASIC (application specific integrated circuit).

In the example shown, the radio unit 6 is included in the detector module 1. In particular, the radio unit 6 is arranged on the module electronics 16 of the detector module 1. However, there are also other embodiment variants, for example, an arrangement on a separate assembly as shown by way of example in FIG. 4.

The housing 3, 11, (e.g., the housing cover 3), has a recess 5 assigned to the detector module 1 for the at least one radio antenna 7, relative to which the radio antenna 7 is arranged, so that wireless data transmission of the detector signals through the housing 3, 11 into an external space is enabled.

Figure 4:
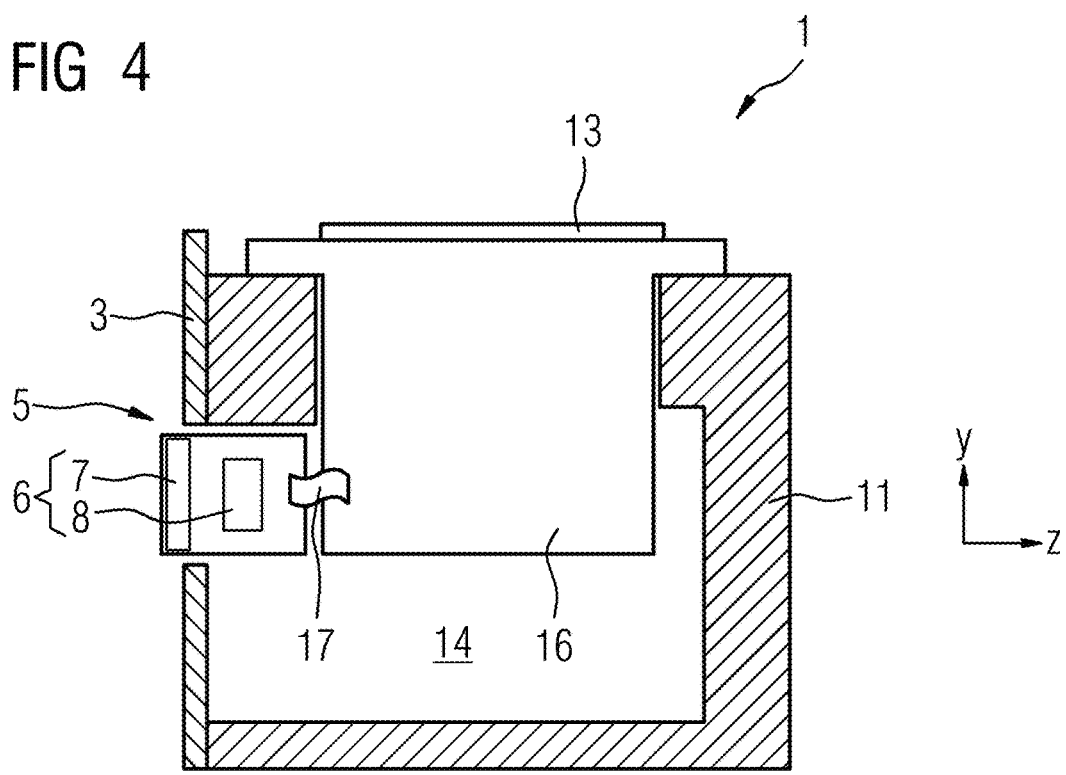
Figure 5:
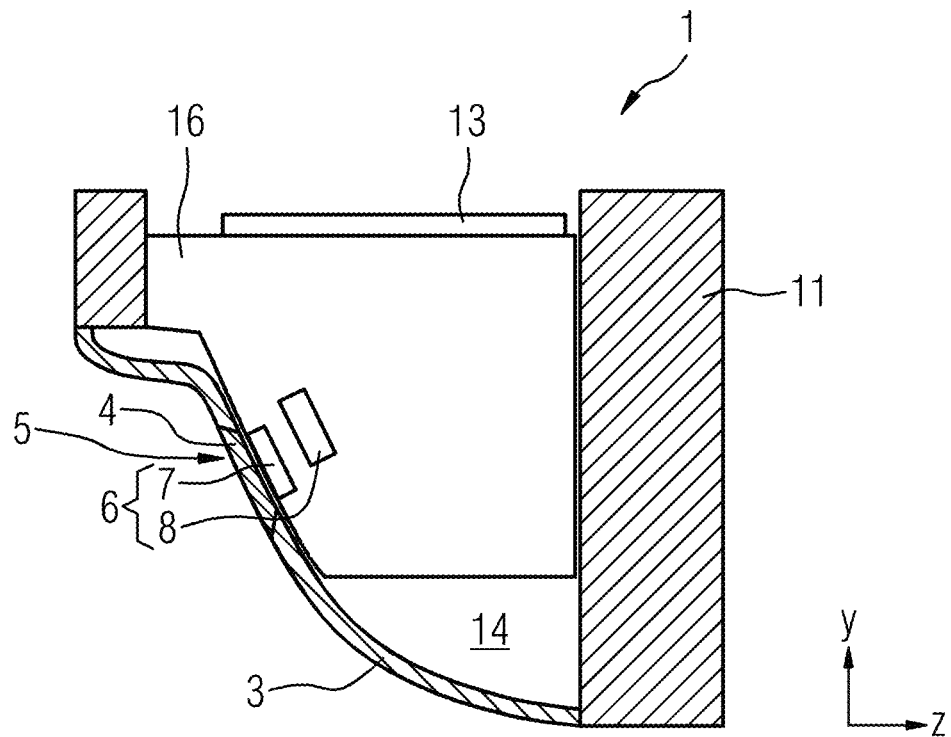

In the case shown, the radio antenna 7 is arranged within the recess 5. However, there may also easily be other embodiment variants, e.g., an arrangement of the radio antenna 7 at least partially outside the housing 3, 11, as shown in FIG. 4, or an arrangement within the housing, as illustrated in FIG. 5. Both examples may also be realized in this embodiment, and vice versa.

The example shown also shows that an area between the radio unit, (e.g., the radio antenna 7), and the housing 3, is electrically sealed by an electrically conductive sealing material 12. For example, this may be configured by a rubber seal or springs. The area relates to a gap between the edge of the recess 5 and an edge of a radio unit 6 positioned relative to it. However, the recess 5 is not covered by the material 12 that would impair wireless data transmission. In other embodiments, however, such a gap is also configured as an air gap, as, for example, in FIG. 4. In a further embodiment, the at least one radio antenna 7 may also be arranged relative to the recess 5 in such a way that the radio antenna has a distance in a sub-mm range (e.g., less than 1 mm) to at least part of the housing 3, so that at least this part of the housing 3 may be used as a ground plane for the radio antenna 7. For example, this arrangement may be achieved by a mechanical assembly made of a dielectric material, which keeps the radio antenna at a tolerated distance relative to the housing 7 in the sub-mm range and also keeps it stable during operation.

In the example shown, the radio unit 6 of the detector module 1 is also protected by parts of the housing 3, 11, (e.g., the module carrier), against incident radiation during operation of the detector apparatus 36, at least along a direction of incidence of the radiation.

FIG. 4 shows an embodiment of a detector apparatus 36 in which, in contrast to the embodiment shown in FIG. 3, the radio unit 6 is arranged on a separate assembly, (e.g., a printed circuit board), which is electrically conductively connected for signal transmission by a flexible cable 17. Furthermore, in the example shown, the radio antenna 7 protrudes through the recess 5 into an external area.

FIG. 5 also shows an embodiment in which, in comparison to the embodiments described above, the radio antenna 7 is arranged within the housing 3, 11, but in the immediate vicinity behind the recess 5.

Furthermore, in this embodiment, one part of the housing, (e.g., the cover plate 3), has a concave shape that curves into the detector interior space 14 of the detector apparatus 36 formed by the housing 3, 11. This makes it possible to optimize the relative arrangement between the housing 3 and the radio unit 6, which is enclosed by the detector module 1. Furthermore, a radiation capability and direction of the radio antenna 7 may be optimized.

In the example shown, a covering of the recess 5 by a material 4 that is permeable for the wireless data transmission of the detector signals is also illustrated. However, such a cover is optional and is configured to the method used and the frequencies employed for wireless data transmission.

A wall thickness taper in a wall area of the housing 3 around the recess 5 is also illustrated in this example. Advantageously, the radiation capability of the radio antenna 7 may be further optimized.

Figure 6:
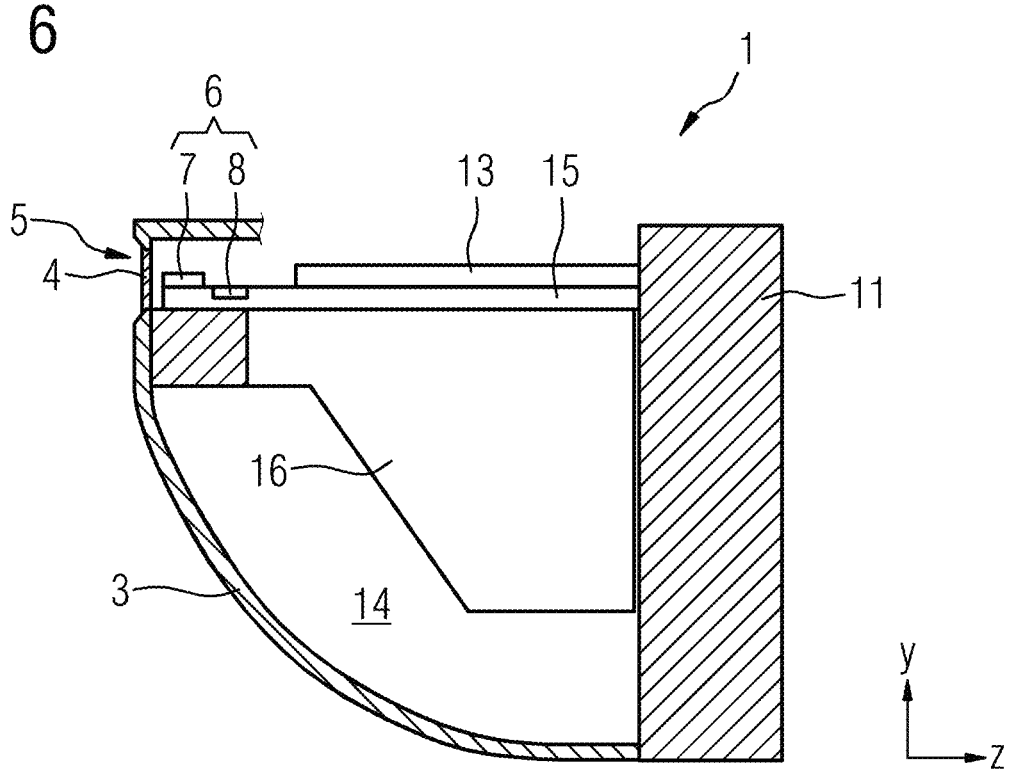

FIG. 6 shows a further embodiment of a detector apparatus 36. In the embodiment shown here, the radio unit 6 is not included of the module electronics 16 of the detector module 1, but of a separate electronic unit 15 of the detector module 1, which in the case shown is provided in a stacked arrangement with the sensor 13. The electronic unit 15 has a surface area that protrudes beyond the planar extent of the sensor and in which the radio unit 6 is arranged. In this way, radio transmission is not hindered by the sensor 13 and sufficient space is created for the radio unit 6, although short cable lengths are still advantageously achieved for signal transmission from the sensor 13 to the radio unit 6.

The electronic unit 15 may be manufactured using what are known as wafer-level packaging methods, in which chips are embedded in polymer encapsulations, e.g., a fan-out wafer-level packaging method, or panel-level packaging methods.

Advantageously, a large number of electronic units 15 with radio circuits 8 already integrated may be provided in a cost-effective and parallelized manner. In this case, the electronic unit 15 thus forms an assembly that includes the radio circuit 8, the housing surrounding the radio circuit and, if necessary, electrically conductive connections for contacting. Due to the larger number of chips that may be processed in parallel, panel-level packaging methods enable a further increase in productivity and the resulting lower package costs. The methods also advantageously offer a very thin package, low thermal resistance, and low interference and inductances due to short electrical connections. The radio antenna 7 may then be applied to the electronic unit 15, for example, lithographically or by a thin-film process.

The corresponding recess 5 is matched to the arrangement of the radio unit 6 on the detector module. A partial area is also provided on the housing 3, which advantageously protects the radio unit 6 from incident radiation.

It is to be understood that the elements and features recited in the appended claims may be combined in different ways to produce new claims that likewise fall within the scope of the present disclosure. Thus, whereas the dependent claims appended below depend on only a single independent or dependent claim, it is to be understood that these dependent claims may, alternatively, be made to depend in the alternative from any preceding or following claim, whether independent or dependent, and that such new combinations are to be understood as forming a part of the present specification.

While the present disclosure has been described above by reference to various embodiments, it may be understood that many changes and modifications may be made to the described embodiments. It is therefore intended that the foregoing description be regarded as illustrative rather than limiting, and that it be understood that all equivalents and/or combinations of embodiments are intended to be included in this description.

The invention claimed is:

1. A detector apparatus for a computed tomography device, the detector apparatus comprising:
   at least one detector module comprising a sensor configured to detect measurement signals;
   at least one radio unit assigned to the at least one detector module, the at least one radio unit having at least one radio antenna for wireless data transmission of the measurement signals; and
   a housing that at least partially encloses the at least one detector module, wherein the housing has a recess for the at least one radio antenna relative to which the at least one radio antenna is arranged, such that the wireless data transmission of the measurement signals through the housing is enabled.

2. The detector apparatus of claim 1, wherein the at least one radio antenna is arranged within the recess or at least partially outside the housing.

3. The detector apparatus of claim 1, wherein the recess is at least partially covered by a material that is permeable for the wireless data transmission of the measurement signals.

4. The detector apparatus of claim 1, further comprising:
   an air gap positioned in an area between the at least one radio unit and the housing.

5. The detector apparatus of claim 1, wherein an area between the at least one radio unit and the housing is electrically sealed by an electrically conductive sealing material.

6. The detector apparatus of claim 1, wherein the at least one radio antenna is arranged relative to the recess in such a way that the at least one radio antenna has a distance in a sub-millimeter range to a part of the housing, such that the part of the housing is configured to be used as a ground plane for the at least one radio antenna.

7. The detector apparatus of claim 6, wherein an area between the at least one radio unit and the housing is electrically sealed by an electrically conductive sealing material.

8. The detector apparatus of claim 1, wherein the at least one radio unit is enclosed by the at least one detector module.

9. The detector apparatus of claim 8, wherein the at least one radio unit is connected to the at least one detector module via a data line.

10. The detector apparatus of claim 8, wherein the at least one radio unit is protected against incident radiation during operation of the detector apparatus at least along a direction of incidence of the radiation.

11. The detector apparatus of claim 1, wherein the at least one radio unit is connected to the at least one detector module via a data line.

12. The detector apparatus of claim 1, wherein the at least one radio unit is protected against incident radiation during operation of the detector apparatus at least along a direction of incidence of the radiation.

13. The detector apparatus of claim 1, wherein at least one part of the housing has a concave shape that curves into a detector interior space of the detector apparatus formed by the housing.

14. The detector apparatus of claim 13, wherein the housing further comprises a wall thickness taper in a wall area around the recess.

15. The detector apparatus of claim 1, wherein the housing further comprises a wall thickness taper in a wall area around the recess.

16. The detector apparatus of claim 1, wherein the at least one detector module is a plurality of detector modules,
   wherein each detector module of the plurality of the detector modules is assigned at least one radio unit and a respective recess in the housing assigned to the respective detector module.

17. A computed tomography device comprising:
   a detector apparatus; and
   an X-ray source in opposition to the detector apparatus, the X-ray source being configured to expose the detector apparatus to X-rays,
   wherein the detector apparatus comprises:
     at least one detector module comprising a sensor configured to detect measurement signals;
     at least one radio unit assigned to the at least one detector module, the at least one radio unit having at least one radio antenna for wireless data transmission of the measurement signals; and
     a housing that at least partially encloses the at least one detector module, wherein the housing has a recess for the at least one radio antenna relative to which the at least one radio antenna is arranged, such that the wireless data transmission of the measurement signals through the housing is enabled.

18. The computed tomography device of claim 17, further comprising:
   at least one receiver unit arranged on a stationary part of the computed tomography device,
   wherein the at least one receiver unit is configured to act together with the at least one radio unit for data transmission.

* * * * *